(12) United States Patent  
Pagani

(10) Patent No.: US 7,619,114 B2  
(45) Date of Patent: Nov. 17, 2009

(54) METHOD FOR THE MODERNIZATION OF A UREA PRODUCTION PLANT

(75) Inventor: Giorgio Pagani, Milan (IT)

(73) Assignee: Urea Casale S.A. (CH)

( * ) Notice: Subject to any disclaimer, the term of this patent is extended or adjusted under 35 U.S.C. 154(b) by 224 days.

(21) Appl. No.: 11/938,473

(22) Filed: Nov. 12, 2007

(65) Prior Publication Data

US 2008/0118414 A1     May 22, 2008

(30) Foreign Application Priority Data

Nov. 20, 2006    (EP)  .................................. 06024016

(51) Int. Cl.
*B01J 8/00* (2006.01)
*B01J 8/04* (2006.01)
*B01J 10/00* (2006.01)
*B01J 10/02* (2006.01)
*F28D 9/00* (2006.01)
*C07C 273/02* (2006.01)
*C07C 273/04* (2006.01)

(52) U.S. Cl. .............................. 564/66; 564/67; 564/70; 564/71; 564/72; 422/187; 422/188; 422/189; 422/196; 422/197; 422/200; 422/201

(58) Field of Classification Search ................. 422/187, 422/188, 189, 196, 197, 200, 201; 564/66, 564/67, 70, 71, 72

See application file for complete search history.

(56) References Cited

FOREIGN PATENT DOCUMENTS

| EP | 1036787 A1 | 9/2000 |
|----|------------|--------|
| EP | 1516664 A1 | 3/2005 |
| WO | 2006/061083 A1 | 6/2006 |

*Primary Examiner*—Peter G O'Sullivan  
(74) *Attorney, Agent, or Firm*—Akerman Senterfitt

(57) ABSTRACT

A method for revamping a urea plant of the type comprising a synthesis section (2) having a urea synthesis reactor (5), a thermal stripping unit (7) and at least one horizontal condensation unit (6), a treatment section (3) operating at medium pressure and a recovery section (4) operating at low pressure foresees the transformation of said at least one horizontal condensation unit (6) into a vertical condensation unit of the submerged type comprising a tube bundle and the provision of means (37, 41) for feeding a flow comprising ammonia and carbon dioxide in vapor phase and a flow of condensation liquid comprising carbamate simultaneously and independently in each of the tubes of said tube bundle with circulation inside said tubes in equicurrent from the bottom towards the top, and means (39, 50) for feeding at least one part of the feed carbon dioxide into said stripping unit (7) for use as stripping agent. Thanks to the present revamping method, the efficiency of the condensation unit (6) is substantially improved, consequently allowing an increase in its capacity and it is possible to leave out the medium pressure treatment section (3) thus obtaining a reduction in energy and maintenance costs.

6 Claims, 4 Drawing Sheets

METHOD FOR THE MODERNIZATION OF A UREA PRODUCTION PLANT

FIELD OF APPLICATION

The present invention refers to a method for revamping a urea production plant according to the thermal stripping process.

in particular, the invention refers to a method for revamping a urea plant of the type comprising:

a urea synthesis reactor;

means for feeding ammonia and carbon dioxide to the reactor for urea synthesis;

a thermal stripping unit for subjecting a reaction mixture comprising urea, carbamate and free ammonia in aqueous solution coming out from the reactor to a partial decomposition treatment of the carbamate and to partial separation of free ammonia, obtaining a flow comprising ammonia and carbon dioxide in vapour phase and a flow comprising urea, residual carbamate and ammonia in aqueous solution;

a section operating at medium pressure for subjecting said flow comprising carbamate, urea and ammonia in aqueous solution to a substantially total separation treatment of the ammonia and partial decomposition of the carbamate;

a recovery section operating at low pressure of a flow comprising urea and residual carbamate obtained in said section operating at medium pressure for the separation of the urea from the carbamate in aqueous solution, at least one horizontal condensation unit for subjecting the flow comprising ammonia and carbon dioxide in vapour phase coming out from the stripping unit to substantially total condensation, obtaining a flow of liquid comprising carbamate in aqueous solution;

means for feeding the flow of liquid comprising carbamate in aqueous solution to the urea synthesis reactor.

In the remainder of the description and in the subsequent claims, the term "revamping" indicates the modification of a pre-existing plant, in order to improve its performance and obtain, for example, an increased production capacity and/or conversion yield, or else a reduction in energy consumption. In particular, the revamping of a urea plant according to the present invention foresees increasing the capacity while preserving the main apparatuses of the high pressure synthesis section (synthesis loop).

In the remainder of the description and in the subsequent claims, the term "horizontal condensation unit" indicates a tube bundle exchanger arranged horizontally in which the condensation of the gaseous phase occurs on the shell side through a condensation liquid (normally a diluted recycled carbamate solution) also fed on the shell side of said exchanger. The condensation heat freed is removed by means of a liquid (normally water) running through the tubes of the tube bundle, said liquid being converted into vapour, by means of the heat exchange.

As known, relative to urea production, there is an increasing need to have, on the one hand, plants of ever-greater capacity and operating efficiency and, on the other hand, ever lower investment and operating costs as well as lower energy consumption.

PRIOR ART

As it is well known, plants of the aforementioned type are widely used to produce urea.

In such plants, the stripping unit is of the tube bundle type with external heating through vapour without additional use of a stripping gas (ammonia or carbon dioxide). In particular, the mixture comprising urea, carbamate and ammonia in aqueous solution coming out from the reactor is made to descend inside the tubes in the form of a film of liquid to which heat is supplied through indirect heat exchange with the vapour flowing outside of the tubes.

The heat supplied by the vapour results in the partial decomposition of the carbamate contained in said mixture into carbon dioxide and ammonia which, together with part of the free ammonia contained in said mixture, are recovered at the top of the stripping unit to be condensed in the condensation unit and then recycled to the synthesis reactor.

Although advantageous from some points of view, the aforementioned urea production plants also have recognised drawbacks.

A first drawback derives from the fact that the efficiency of the thermal stripping in the high pressure stripping unit is not optimal, above all in terms of the removal of ammonia, with the consequence that the aqueous solution comprising urea and residual carbamate coming out from the stripping unit also contains a substantial amount of free ammonia.

This necessarily means that the medium pressure treatment section must be sufficiently developed with the provision in particular, in said section, of at least one distillation column to which said solution coming out from the stripping unit is sent, and a rectifying column of suitable capacity for recovering the ammonia from the vapours obtained in said distillation unit.

In this way, indeed, ammonia to be recycled to the synthesis reactor can be recovered (in order to obtain an acceptable production yield) and an aqueous solution comprising urea and residual carbamate and substantially free of ammonia can be obtained which can be effectively treated in the urea recovery section according to the usual urea separation and recovery operations.

Another drawback of the aforementioned plants lies in the limited capacity of the high pressure condensation unit.

In order to avoid or at least reduce as much as possible the aforementioned drawbacks, it has been proposed up to now methods for revamping the aforementioned plants that foresee the insertion of additional apparatuses and/or the increase of the existing ones in the medium pressure treatment section in order to effectively recover in particular ammonia from the aqueous solution coming out from the high pressure stripping unit as well as the insertion in parallel of an additional condensation unit to increase the capacity of the condensation section.

However, such measures have a very negative influence both in terms of investment costs and in terms of the complexity of construction deriving from the revamping of the condensation section and of the medium pressure treatment section according to the aforementioned methods of the prior art.

Due to these drawbacks, the revamping of urea production plants according to the thermal stripping process has up to now had a relatively modest application, despite the ever-increasing interest of the industry in modifying existing plants—instead of replacing them with new plants—in order to increase the production capacity and decrease the energy consumption.

SUMMARY OF THE INVENTION

The technical problem forming the basis of the present invention is therefore to provide a method for revamping a urea production plant according to the thermal stripping process that allows an increase in its production capacity and involves low energy consumption together with low investment costs and that is technically simple to carry out.

In accordance with the present invention, this problem is solved by a method of the type indicated above, which is characterised in that it comprises the steps of:

transforming said at least one horizontal condensation unit into at least one vertical condensation unit of the "submerged" type, providing means for feeding said flow comprising ammonia and carbon dioxide in vapour phase and said condensation liquid comprising carbamate simultaneously and independently in each of the tubes of the tube bundle of said vertical condensation unit with circulation of said flow comprising ammonia and carbon dioxide in vapour phase and said condensation liquid comprising carbamate inside said tubes in equicurrent from the bottom towards the top, and providing means for feeding at least one part of the carbon dioxide feed into said stripping unit for use as stripping agent of said reaction mixture comprising urea, carbamate and free ammonia in aqueous solution coming out from the reactor.

In the remainder of the description and in the subsequent claims, the term "vertical condensation unit of the submerged type" indicates an apparatus in which the liquid phase fills (submerges) the tube bundle and where the condensation of the gaseous phase occurs passing through such a liquid phase.

Thanks to the present invention, the vertical position and the size of the existing condensation unit are exploited, which, once transformed, ensures a high liquid head (height) inside the tubes for the condensation of the gaseous phase coming out from the stripping unit.

Moreover, since the gaseous phase to be condensed is fed independently in all of the tubes of the tube bundle, an effective mixing of the gaseous phase in the liquid phase is achieved, so obtaining a substantial increase in the exchange coefficient inside the tubes and thus consequently increasing the global exchange coefficient and the efficiency of the pre-existing condensation section.

This allows to increase the capacity of the existing condensation section.

Moreover, thanks to the presence of a high liquid head in the tubes of the modified condensation unit according to the invention and the circulation of the liquid phase from the bottom towards the top it is possible to increase the residence time for carbamate, which can thus react partially converting into urea, in a simple and effective way.

By doing so, a substantial increase of the urea produced in the condensation unit is obtained, to the great advantage of the greater capacity of the plant.

Experimental results have demonstrated that with the modified condensation unit according to the invention it is possible to obtain about 30% or more of the overall urea produced by the plant in said condensation unit.

Moreover, it should be noted that with the revamping method according to the invention the stripping of the mixture comprising urea, carbamate and free ammonia in aqueous solution coming out from the reactor is carried out not only thermally, using the heat supplied by the heating fluid, but also using at least part of the carbon dioxide feed as stripping agent.

This advantageously allows the efficiency of the stripping to be substantially increased and in particular it is possible to substantially reduce the ammonia content in the aqueous urea solution coming out from the stripping unit.

The advantages resulting from the above are clear and at the same time considerable since, with the revamping method according to the invention, it is possible to substantially simplify or even by-pass the apparatuses of the medium pressure treatment section—with particular reference to the distillation column and to the rectifying column for the recovery of the ammonia—thus obtaining a reduction in energy consumption and in maintenance costs.

More specifically, experimental results have demonstrated that with the modified plant according to the revamping method of the invention it is possible to drastically reduce the ammonia content in the aqueous urea solution coming out from the stripping unit to the extent that it is possible to dispense with the medium pressure treatment section and send said solution directly to the low pressure recovery section for the usual urea separation and recovery operations.

Obviously, this does not rule out the possibility of continuing to use the medium pressure treatment section of the pre-existing plant in the case in which it is still advantageous to recover ammonia from the aqueous urea solution coming out from the stripping unit. However, since with the revamping according to the invention the amount of ammonia to be recovered is substantially lower, such a medium pressure treatment section not only does not need increase but can advantageously be used at reduced operating speed, thus in any case achieving a reduction in energy costs with respect to those involved in the pre-existing operation of the plant.

According to an aspect of the revamping method of the present invention, the step of providing means for feeding the flow comprising ammonia and carbon dioxide in vapour phase and said condensation liquid to the tube bundle comprises the operations of:

providing a gas distributor close to the bottom end of said tube bundle in fluid communication with the means for feeding said flow comprising ammonia and carbon dioxide in vapour phase to said vertical condensation unit, providing a plurality of connection ducts that extend from said distributor inside said tubes for directly feeding said flow comprising ammonia and carbon dioxide in vapour phase in each of said tubes.

In this way, it is advantageously possible to homogeneously and uniformly distribute the gaseous phase to be condensed in each of the tubes of the tube bundle where said liquid phase comes into contact with the condensation liquid, to the great advantage of an improved heat exchange coefficient and of a greater condensation yield.

In accordance with another aspect of the revamping method according to the present invention, the vertical condensation unit of the submerged type is arranged in raised position with respect to the reactor and the stripping unit.

Such an arrangement, with a non-excessive investment to foresee a suitable support structure for the raised condensation unit, advantageously allows the height of the vertical condensation unit to be adjusted with respect to the reactor and to the condenser so as to make the flow of carbamate solution coming out from the condensation unit flow by gravity to the synthesis reactor and to make the flow of aqueous solution comprising urea and carbamate obtained from it flow to the stripping unit.

On the other hand, in the case one wishes to arrange (or keep) the condensation unit substantially at the same height as the reactor and the condenser, the revamping method according to the invention also foresees the step of:

providing means for pumping said flow of liquid comprising carbamate in aqueous solution from said vertical condensation unit to said reactor.

According to a further aspect of the present invention, the revamping method is characterised in that it also comprises the step of:

providing means for feeding a flow comprising urea and residual carbamate in aqueous solution from said stripping unit to said low pressure urea recovery section.

In this way, during the operation of the modernised plant according to the invention, it is possible to advantageously bypass the medium pressure treatment section, feeding the flow of aqueous urea solution coming out from the stripping unit directly to the urea recovery section.

According to a further aspect of the present invention, the revamping method is characterised in that it also comprises the steps of:

providing means for feeding the totality of the carbon dioxide feed into said stripping unit for use as stripping agent of said reaction mixture comprising urea, carbamate and free ammonia in aqueous solution coming out from the reactor, providing means for feeding a minority portion of said flow comprising ammonia and carbon dioxide in vapour phase coming out from said stripping unit directly to said reactor for urea synthesis;

providing means for feeding a majority portion of said flow comprising ammonia and carbon dioxide in vapour phase coming out from said stripping unit to said at least one condensation unit.

By majority portion we mean to indicate a portion that is greater than 50% of the total flow of ammonia and carbon dioxide in vapour phase coming out from the stripping unit. According to the operating conditions in the synthesis reactor, the majority portion can be between 65-85% of such a flow, for example between 70-75%.

Thanks to the fact that the totality of the carbon dioxide is fed into the stripping unit (in the case in which the existing stripping unit has a high capacity or is replaced—for example because it has reached the end of its useful life—with a new stripping unit with greater capacity) and the fact that means are foreseen to divide the flow comprising ammonia and carbon dioxide in vapour phase (coming from the stripping unit) into a minority portion and a majority portion, an optimal efficiency of condensation of the majority part of the gaseous phase sent to the vertical condensation unit with formation of urea in said condensation unit, an effective control of the reaction temperature inside the synthesis reactor (thermal balance) by means of the minority portion of the gaseous phase that is sent directly from the stripping unit to the reactor and a reduction of the inert gas content in the reactor that usually accompanies the feed flow of carbon dioxide are at the same time obtained, giving the advantage of a better urea production yield in said reactor.

Advantageously, the present invention allows the exchange coefficient and therefore the efficiency of the condensation section to be substantially increased, allowing a debottleneck of the existing plant to the advantage of the global production capacity that can thus be optimally increased.

All of this is achieved simply and efficiently, with minimal and totally marginal interventions in the high pressure synthesis section that is thus substantially kept unaltered, and with low energy consumption.

It follows from this that the investment, installation and operating costs are substantially lower if compared to the costs required with revamping methods according to the prior art.

Indeed, thanks to the present method, the pre-existing condensation section is neither increased nor replaced with new apparatuses but rather is advantageously preserved, requiring just slight internal modifications of the condensation unit(s) so as to obtain a more efficient condensation of the gaseous phase fed into it and, moreover, the medium pressure treatment section not only is not increased but can be left out thus obtaining a substantial reduction in energy and maintenance costs.

It is important to observe how contrary to the constant teaching of the prior art that, in plants with thermal stripping technology, suggests boosting the condensation section and the medium pressure treatment section by adding new apparatuses (e.g. new condensation units) or by replacing existing apparatuses with others of greater capacity, the revamping method according to the present invention allows the same (if not larger) increases in capacity to be obtained with the existing apparatuses, by intervening marginally, in particular on the condensation unit(s), from the structural point of view, but drastically in terms of its/their way of operating.

This is a totally surprising result if one considers that in accordance with the revamping methods according to the prior art it was unthinkable to be able to obtain substantial increases in capacity in the condensation section and in the medium pressure treatment section with just the existing apparatuses.

Further characteristics and advantages of the present finding shall become clearer from the following description of some example embodiments of the revamping method according to the invention, given for indicating and not limiting purposes, with reference to the attached drawings.

DETAILED DESCRIPTION OF A PREFERRED EMBODIMENT

Figure 1:
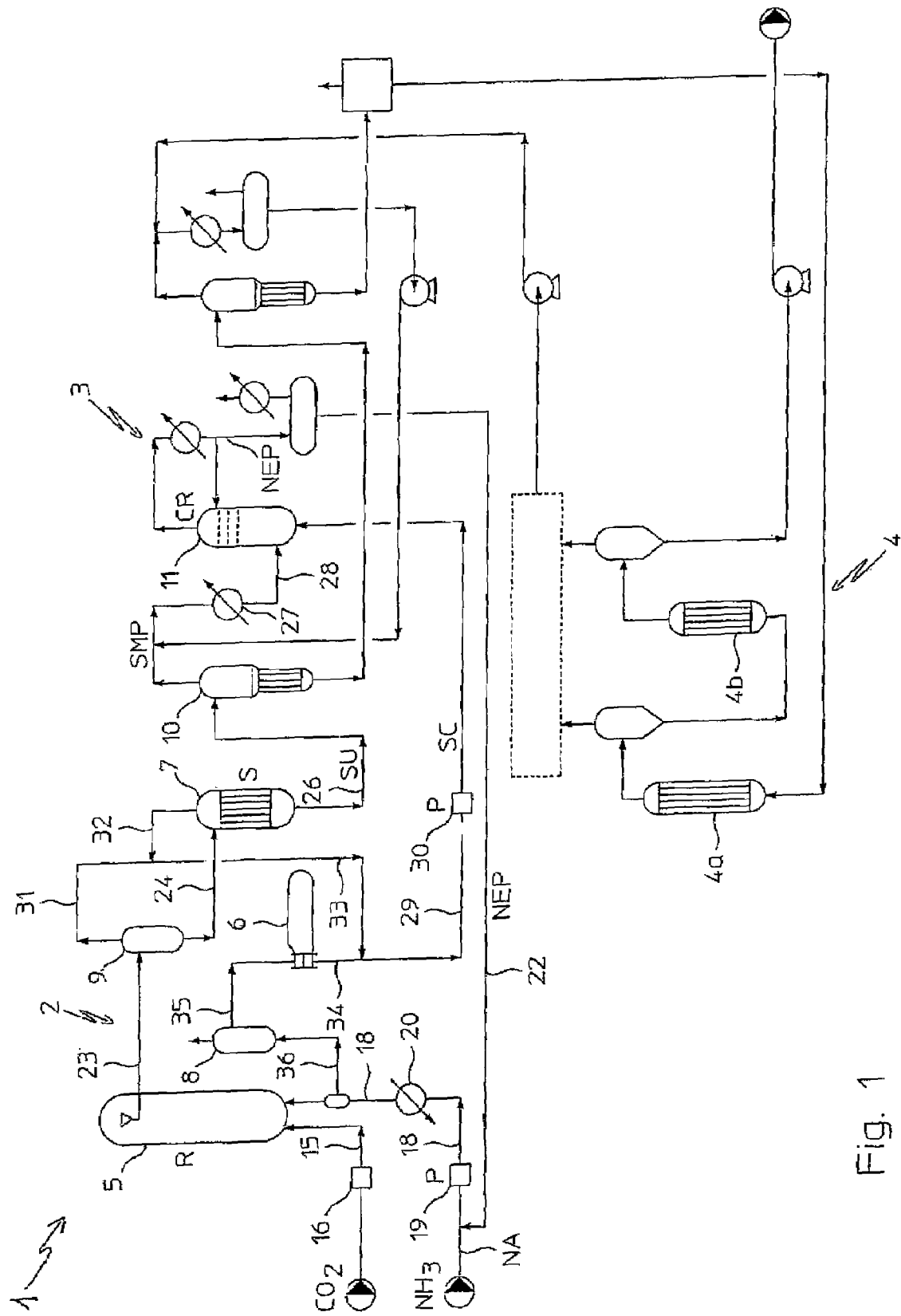
FIG. 1 schematically and partially illustrates a urea production plant according to the thermal stripping process in accordance with the prior art.

With reference to FIG. 1, a urea production plant according to the thermal stripping process in accordance with the prior art is schematically and partially represented, said plant being globally indicated with 1.

With the aim of simplifying the presentation of the present invention we shall refer specifically just to those parts of the plant 1 and to the connection ducts between parts of said plant, described hereafter and illustrated in FIG. 1, which are strictly necessary to understand the present invention.

The plant 1 comprises a synthesis section 2 (synthesis loop) operating at high pressure (120-150 bars) a treatment section 3 operating at medium pressure (15-25 bars) and a urea recovery section 4 operating at low pressure, said sections being in fluid communication with each other.

The synthesis section 2 comprises a reactor 5, a condensation unit 6 and a stripping unit 7 operating at substantially the same pressure as well as a first scrubber 8 and a second scrubber 9. The condensation unit 6 is of the horizontal type with a tube bundle in which the gaseous phase to be condensed together with the condensation liquid flow from the shell side whereas the condensation heat is recovered by means of a liquid (e.g. water) flowing inside the tubes that, through the heat exchange, is converted into vapour. The stripping unit 7 operates according to thermal stripping technology and is in particular of the film type with external heating through vapour. In accordance with such a technology, the solution comprising carbamate to be subjected to stripping is made to run in the form of a liquid film inside the tubes of a tube bundle foreseen in said stripping unit 7 whereas the vapour that flows outside of the tubes supplies the heat necessary to carry out the decomposition of carbamate from which ammonia and carbon dioxide are obtained that are recovered at the top of the stripping unit 7.

The medium pressure treatment section 3 comprises a series of per se conventional apparatuses, including a distillation unit 10 and a rectifying column 11 for the recovery of ammonia in fluid communication with each other. The section 3 also comprises other per se conventional apparatuses that are not described here since it is not necessary for the understanding of the present invention. In the same way, the low pressure treatment section 4 comprises a series of per se conventional apparatuses, including a first still 4a and a second still 4b both operating under vacuum, which are not described further here since it is not necessary for the understanding of the present invention.

Respective means for feeding the various flows to the apparatuses of the urea production plant 1 are generally indicated with 15-36 in FIG. 1.

Such feeding means comprise connection pipes or ducts, pumps, compressors, ejectors and other known apparatuses, normally used in this type of plant, and therefore they shall not be described in greater detail in the remainder of the description.

In general, in the present description and in the subsequent claims, and unless indicated otherwise, by feeding, connection or extraction means we mean to indicate pipes, ducts, pumps, compressors, ejectors or other known apparatuses, which are used to transport a liquid or gaseous fluid from one place to another in the plant.

In accordance with a way of operating the prior art plant 1, the carbon dioxide feed is sent totally to the synthesis reactor 5 through means 15 after having been suitably compressed by means of a compressor 16. Similarly, the liquid synthesis ammonia is fed to the reactor 5 through means 18 and a pump 20 and with prior preheating in an exchanger 20. The "fresh" feed ammonia is added to with a flow of recovery ammonia coming from the medium pressure treatment section 3 through feeding means 22, as shall be made clear in the remainder of the description. The urea synthesis is carried out in the reactor 5, obtaining a flow consisting of an aqueous solution comprising urea, carbamate and free ammonia. Such a solution is sent to the scrubber 9 through feeding means 23 for the separation of a gaseous flow comprising carbon dioxide, ammonia and possible inert gases (usually added to the flow of carbon dioxide feed to protect the apparatuses from corrosion) and from here to the stripping unit 7 through means 24. In the stripping unit 7, the aforementioned solution is subjected to partial decomposition of the carbamate contained in it through heat supplied by vapour, obtaining a gaseous flow comprising ammonia and carbon dioxide and a liquid flow consisting of an aqueous solution comprising urea, residual carbamate and ammonia. The flow of aqueous solution coming out from the stripping unit 7 is sent through means 26 to the distillation unit 10 of the medium pressure treatment section 3. Without going into detail about the operation of the medium pressure treatment section 3, which is per se conventional, a further gaseous flow comprising ammonia and carbon dioxide and a flow consisting of an aqueous solution essentially comprising urea and residual carbamate are obtained from the distillation unit 10. The gaseous flow coming out from the distillation unit 10 is sent through means 27 and 28 to the rectifying column 11 whereas the flow of aqueous solution coming out from said distillation unit 10 is subjected to further per se conventional treatments in the other apparatuses of the medium pressure treatment section 3 for the recovery of carbamate contained in it. At the end of such treatments, a flow consisting of a solution comprising urea and a low content of carbamate is obtained, which is sent from the medium pressure treatment section 3 to the low pressure section 4 for the conventional urea recovery operations.

Going back to the distillation unit 10, the gaseous flow comprising ammonia and carbon dioxide obtained in it is mixed with a flow consisting of a recycled carbamate solution obtained further downstream in the medium pressure treatment section 3 and the resulting mixture is subjected to heat exchange (cooling) in an exchanger 27 and fed from it through means 28 to the rectifying column 11. In the rectifying column 11, ammonia is recovered from such a mixture in a per se conventional way obtaining a gaseous flow of high purity ammonia and a carbamate solution.

The gaseous flow of ammonia coming out from the rectifying column 11 is then suitably condensed through a series of per se conventional cooling and compression stages and recycled through the aforementioned means 22 to the flow of ammonia feed to the reactor 5.

The flow of carbamate solution obtained from the rectifying column 11 is, on the other hand, recycled through means 29 and a pump 30 to the horizontal condensation unit 6 of the high pressure synthesis section 2.

Such a condensation unit also receives the gaseous flow comprising carbon dioxide, ammonia and inert gases coming out from the scrubber 9 and the gaseous flow comprising ammonia and carbon dioxide coming out from the stripping unit 7.

In particular, the aforementioned gaseous phases are mixed together through the means 31 and 32 and the resulting gaseous mixture is mixed through the means 33 with the flow of carbamate solution coming from the rectifying column 11 obtaining a liquid/gas mixture that, through the means 34, is fed to the horizontal condensation unit 6.

In the unit 6, the gases (with the exception of the inerts) are subjected to substantially total condensation through the carbamate solution (which acts as condensation liquid) on the shell side and the condensation heat is removed through a liquid (e.g. water) passing through the tubes of the unit 6.

At the outlet from the condensation unit 6 a flow is thus obtained consisting of a carbamate solution that is fed through the means 35 to the scrubber 8 for the separation of inerts and from here to the synthesis reactor 5 through the means 36.

Figure 2:
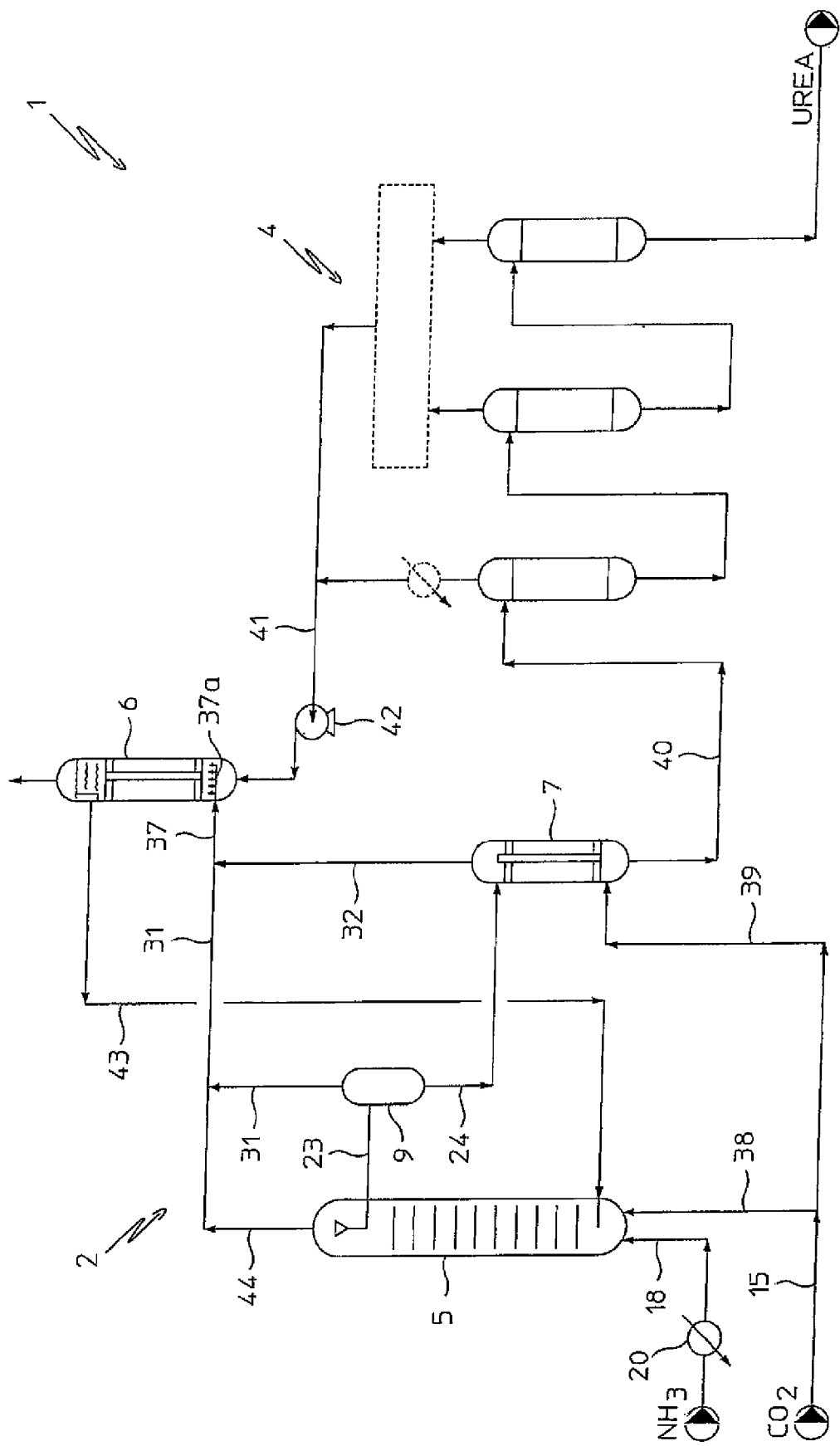
FIG. 2 schematically and partially illustrates a urea production plant according to the stripping process with carbon dioxide carried out by revamping the plant of FIG. 1 in accordance with a preferred embodiment of the revamping method according to the invention.

With reference to FIG. 2, the urea production plant of FIG. 1 is advantageously represented, suitably modified in accordance with a first embodiment of the revamping method according to the present invention. For the sake of simplicity, the medium pressure treatment section 3 has been left out since it is not relevant for the purposes of the following description of the invention.

In FIG. 2, the details of the plant 1 that are structurally and functionally equivalent to those illustrated in FIG. 1 shall be indicated with the same reference numerals and shall not be described any further.

Thanks to the revamping method, the condensation unit 6 is arranged with vertical layout and the means for feeding the gaseous flow comprising ammonia and carbon dioxide in vapour phase coming out from the stripping unit 3 and the condensation liquid flow (recycled carbamate solution) to the condensation unit 6 are suitably modified so as to feed said gaseous flow and said liquid flow simultaneously and independently into each of the tubes of the tube bundle with circulation inside said tubes in equicurrent from bottom to top.

Moreover, the means for feeding carbon dioxide are modified so as to send a part of it to the stripping unit 7 for use as stripping agent of the reaction mixture comprising urea, carbamate and free ammonia in aqueous solution coming out from the reactor 5.

For this purpose, in accordance with the embodiment of FIG. 2, the means 33 of the existing plant of FIG. 1 are modified and means 37 for feeding the gaseous flow to be condensed to the condensation unit 6 separately from the flow of condensation liquid are arranged.

Moreover, the condensation unit 6 is modified on the inside by arranging a gas distributor (shown schematically with reference numeral 37a) close to the bottom end of the tube bundle in fluid communication with the means 37 for feeding the gaseous flow to be condensed to said vertical condensation unit 6 and arranging a plurality of connection ducts (not shown) that extend from said distributor inside the tubes of the tube bundle for directly feeding said gaseous flow to be condensed into each of said tubes.

As far as the feeding of carbon dioxide is concerned, the means 15 are modified and means 38 for feeding a portion of said carbon dioxide to the reactor 5 for thermal balancing the urea synthesis reaction and means 39 for feeding a remaining portion of said carbon dioxide to the stripping unit 7 are arranged.

Advantageously, the carbon dioxide fed to the stripping unit 7 flows inside the tubes of the tube bundle in countercurrent to the descending film of the aqueous solution coming from the reactor 5 substantially improving the efficiency of the stripping and the recovery of ammonia and carbon dioxide from said solution.

In particular, in accordance with the revamping method according to the invention, the aqueous solution obtained by the stripping advantageously possesses a very low ammonia content such as to make the ammonia recovery treatments in the medium pressure section unnecessary.

Therefore, in accordance with the present embodiment of the revamping method according to the invention, means 40 for sending the flow of aqueous solution coming out from the stripping unit 7 essentially comprising urea and carbamate directly to the urea recovery section 4 are arranged. In this way, advantageously, the medium pressure treatment section can be by-passed achieving a substantial saving in energy and maintenance costs of the relative apparatuses.

Moreover, by excluding the medium pressure treatment section 3 from the operation of the plant 1, the revamping method according to the invention foresees the modification of the means 29 and 30 for recycling the carbamate solution from said medium pressure treatment section 3 to the condensation unit 6.

For this purpose, means 41 and 42 (for example a duct 41 and a pump 42) are arranged to place the aforementioned condensation unit 6 in fluid communication with the urea recovery section 4 in order to use a recycled carbamate solution obtained in said urea recovery section 4 as condensation liquid in the unit 6.

It should also be noted that in accordance with the present embodiment of the revamping method of the invention, the scrubber 8 for the separation of a gaseous component from the carbamate solution obtained in the condensation unit 6 is advantageously by-passed and means 43 for feeding said carbamate solution directly to the synthesis reactor 5 are arranged.

Moreover, the condensation unit 6 is advantageously arranged in raised position with respect to the reactor 5 and to the stripping unit 7. Advantageously, the height at which the condensation unit 6 is arranged is selected so as to obtain a natural circulation (by gravity) of the carbamate solution coming out from the condensation unit 6 to the synthesis reactor 5 and of the aqueous solution comprising urea, carbamate and free ammonia obtained from here to the stripping unit 7.

It should also be noted in the present embodiment of the revamping method according to the invention that it is foreseen the separation of a gaseous flow comprising ammonia, carbon dioxide and insert gases from the synthesis reactor 5 and therefore it is foreseen to have means for feeding said gaseous flow coming out from the reactor to the condensation unit 6 after prior mixing with the gaseous flow coming from the scrubber 9 and the gaseous flow coming from the stripping unit 7.

According to another embodiment of the revamping method according to the invention (not shown), the scrubber 9 can also be by-passed. In this case, the revamping method according to the invention foresees the modification of the feeding means 24 and 31 and the provision of means for feeding the flow of aqueous solution comprising urea, carbamate and free ammonia coming out from the synthesis reactor 5 directly to the stripping unit 7.

Figure 3:
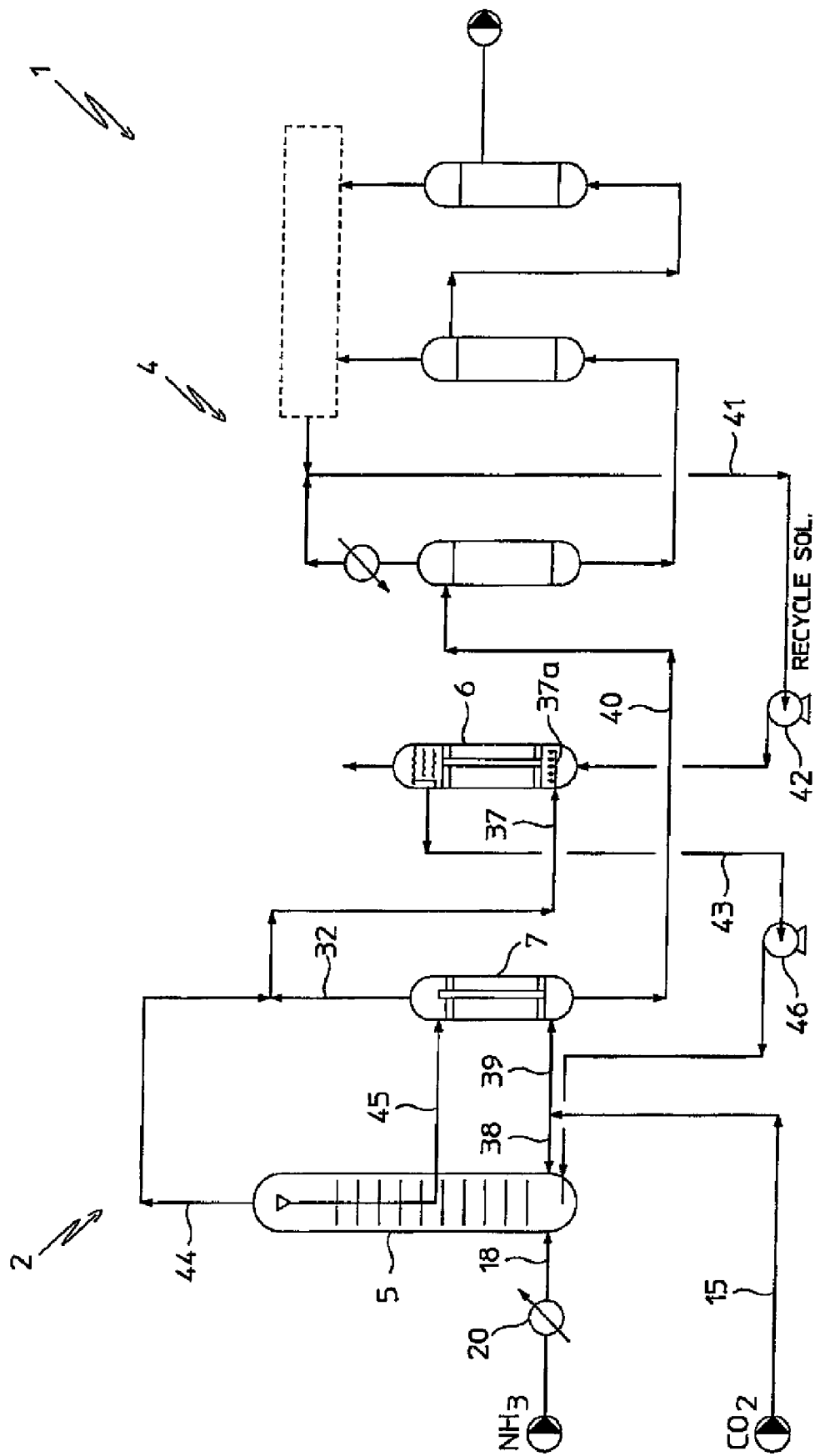
FIG. 3 schematically and partially illustrates a urea production plant according to the stripping process with carbon dioxide carried out by revamping the plant of FIG. 1 in accordance with another preferred embodiment of the revamping method according to the invention.

FIG. 3 once again shows the plant 1 (with the medium pressure treatment section left out for the sake of simplicity) suitably modified according to another way of carrying out the revamping method of the invention.

In accordance with such an embodiment, the horizontal condensation unit 6 of the existing plant 1 is structurally modified as described previously but is now arranged substantially at the same height as the reactor 5 and the stripping unit 7. It follows from this that, in accordance with this embodiment of the revamping method of the invention, a pump 46 for the circulation through the means 43 of the flow of carbamate solution coming out from the condensation unit 6 to the synthesis reactor 5 is arranged.

Moreover, the same modifications already described previously with reference to FIG. 2 are carried out regarding the feeding of the carbon dioxide now sent in part to the reactor 5 for the thermal balancing of the synthesis reaction and in part to the stripping unit 7. It should also be noted that the scrubber 9 is left out and the means 24 and 31 are modified by arranging means 45 for feeding the flow of aqueous solution comprising urea, carbamate and free ammonia coming out from the reactor 5 directly to the stripping unit 7.

FIG. 4 once again shows the plant 1 (with the medium pressure treatment section left out for the sake of simplicity) suitably modified according to a further way of carrying out the revamping method of the invention.

Figure 4:
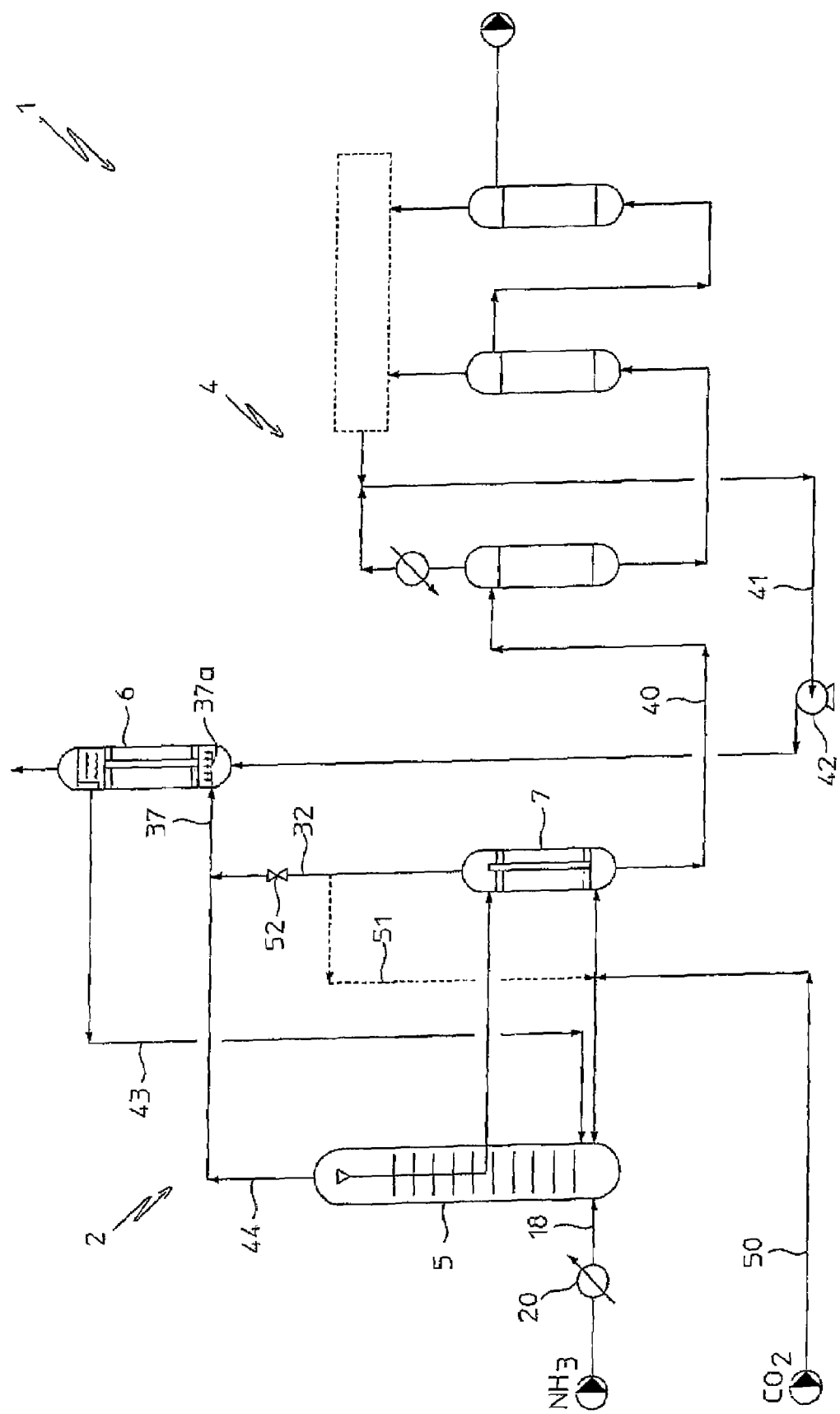
FIG. 4 schematically and partially illustrates a urea production plant according to the stripping process with carbon dioxide carried out by revamping the plant of FIG. 1 in accordance with a further preferred embodiment of the revamping method according to the invention.

In FIG. 4, the details of the plant 1 that are structurally and functionally equivalent to those illustrated in the previous figures shall be indicated with the same reference numerals and shall not be described any further.

In such an embodiment of the revamping method according to the invention, the means 18 for feeding carbon dioxide are modified by arranging means 50 for feeding the totality of the flow of carbon dioxide to the stripping unit 7.

Moreover, means 51 for feeding a minority portion of the flow comprising ammonia and carbon dioxide in vapour phase coming out from the stripping unit 7 directly to the synthesis reactor 5 are provided, whereas a majority portion of said flow comprising ammonia and carbon dioxide in vapour phase coming out from said stripping unit 7 is fed to the condensation unit 6 through the aforementioned means 32 and 37 after prior mixing with the gaseous flow coming out from the synthesis reactor 5 and directed towards said condensation unit 6 through the means 44. A control valve 52 for controlling the majority portion and the minority portion of the gaseous flow comprising ammonia and carbon dioxide is also provided.

In accordance with such an embodiment of the invention, the plant 1 is also modified as already described previously with reference to FIG. 2 with the further exclusion of the scrubber 9 as described previously with reference to FIG. 3.

The advantages obtained with the revamping method according to the present invention are many. In particular, it is worth to point out that with such a revamping it is possible to obtain at the same time, in a simple and efficient way, a high exchange coefficient in the condensation unit 6, high conversion yields and therefore a high production capacity. Moreover, it is possible to leave out the medium pressure treatment section of a plant operating with thermal stripping technology thus substantially reducing the energy and maintenance costs. All of this is achieved by intervening minimally on the existing apparatuses, thus keeping the investment costs for such interventions low.

Lastly, the scope of protection defined by the revamping method according to the present invention should be considered to extend—as well as to the modification of existing structures—also to the particular case of replacement due to wear of the existing condensation unit with a new unit having a configuration of the type described previously with reference to FIGS. 2-4. This particular case comes about where the existing unit is at the end of its operating life, i.e. it no longer ensures reliable and long-lasting operation.

The invention claimed is:

1. Method for revamping a urea plant of the type comprising:
   a urea synthesis reactor;
   means for feeding ammonia and carbon dioxide to the reactor for urea synthesis;
   a thermal stripping unit for subjecting a reaction mixture comprising urea, carbamate and free ammonia in aqueous solution coming out from the reactor to a partial decomposition treatment of the carbamate and partial separation of the free ammonia, obtaining a flow comprising ammonia and carbon dioxide in vapour phase and a flow comprising urea, residual carbamate and ammonia in aqueous solution;
   a section operating at medium pressure for subjecting said flow comprising carbamate, urea and ammonia in aqueous solution to a substantially total separation treatment of the ammonia and partial decomposition of the carbamate;
   a recovery section operating at low pressure of a flow comprising urea and residual carbamate obtained in said section operating at medium pressure for the separation of the urea from the carbamate in aqueous solution,
   at least one horizontal condensation unit for subjecting the flow comprising ammonia and carbon dioxide in vapour phase coming out from the stripping unit to substantially total condensation, obtaining a flow of liquid comprising carbamate in aqueous solution;
   means for feeding the flow of liquid comprising carbamate in aqueous solution to the urea synthesis reactor;
said revamping method being characterised in that it comprises the steps of:
   transforming said at least one horizontal condensation unit into a vertical condensation unit of the "submerged" type, comprising a tube bundle having a plurality of tubes for the condensation of carbamate,
   providing means for feeding said flow comprising ammonia and carbon dioxide in vapour phase and said condensation liquid comprising carbamate simultaneously and independently in each of the tubes of said tube bundle of said vertical condensation unit with circulation of said flow comprising ammonia and carbon dioxide in vapour phase and said condensation liquid comprising carbamate inside said tubes in equicurrent from the bottom towards the top, and
   providing means for feeding at least one part of the feed carbon dioxide into said stripping unit for use as stripping agent of said reaction mixture comprising urea, carbamate and free ammonia in aqueous solution coming out from the reactor.

2. Revamping method according to claim 1, wherein said step of providing means for feeding said flow comprising ammonia and carbon dioxide in vapour phase and said condensation liquid to the tube bundle comprises the further operations of:
   providing a gas distributor close to the bottom end of said tube bundle in fluid communication with the means for feeding said flow comprising ammonia and carbon dioxide in vapour phase to said vertical condensation unit,
   providing a plurality of connection ducts that extend from said distributor inside said tubes for directly feeding said flow comprising ammonia and carbon dioxide in vapour phase in each of said tubes.

3. Revamping method according to claim 1, wherein said vertical condensation unit of the submerged type is arranged in raised position with respect to said reactor and to said stripping unit.

4. Revamping method according to claim 1, wherein:
   arranging said vertical condensation unit of the submerged type at substantially the same height as said reactor and said stripping unit, and
   providing means for pumping said flow of liquid comprising carbamate in aqueous solution from said vertical condensation unit to said reactor.

5. Revamping method according to claim 1, wherein it also comprises the step of:
   providing means for feeding a flow comprising urea and residual carbamate in aqueous solution from said stripping unit to said low pressure urea recovery section.

6. Revamping method according to claim 1, wherein it also comprises the steps of:

providing means for feeding the totality of the carbon dioxide feed into said stripping unit for use as stripping agent of said reaction mixture comprising urea, carbamate and free ammonia in aqueous solution coming out from the reactor, providing means for feeding a minority portion of said flow comprising ammonia and carbon dioxide in vapour phase coming out from said stripping unit directly to said reactor for urea synthesis;

providing means for feeding a majority portion of said flow comprising ammonia and carbon dioxide in vapour phase coming out from said stripping unit to said condensation unit.

* * * * *